US012599396B2

(12) United States Patent 
Ashiba et al.

(10) Patent No.: US 12,599,396 B2 
(45) Date of Patent: Apr. 14, 2026

(54) ULTRASONIC TREATMENT INSTRUMENT

(71) Applicant: OLYMPUS MEDICAL SYSTEMS CORP., Tokyo (JP)

(72) Inventors: Hiroshi Ashiba, Tokorozawa (JP); Yasuhiro Maeda, Tokyo (JP); Minoru Katsumata, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 334 days.

(21) Appl. No.: 18/448,669

(22) Filed: Aug. 11, 2023

(65) Prior Publication Data

US 2023/0380856 A1     Nov. 30, 2023

Related U.S. Application Data

(63) Continuation of application No. PCT/JP2021/007980, filed on Mar. 2, 2021.

(51) Int. Cl.
*A61B 17/32*          (2006.01)

(52) U.S. Cl.
CPC ................. *A61B 17/320068* (2013.01); *A61B 2017/320089* (2017.08)

(58) Field of Classification Search
CPC ............ A61B 17/320068; A61B 2017/320089
See application file for complete search history.

(56) References Cited

U.S. PATENT DOCUMENTS

| | | | |
|---|---|---|---|
| 5,897,523 | A | 4/1999 | Wright et al. |
| 6,090,120 | A | 7/2000 | Wright et al. |
| 2004/0138570 | A1 | 7/2004 | Nita et al. |
| 2009/0216157 | A1 | 8/2009 | Yamada |
| 2010/0168741 | A1 | 7/2010 | Sanai et al. |

FOREIGN PATENT DOCUMENTS

| | | |
|---|---|---|
| JP | 2009195676 A | 9/2009 |
| WO | WO-2004064677 A2 | 8/2004 |
| WO | WO-2010076873 A1 | 7/2010 |
| WO | WO-2017119099 A1 | 7/2017 |

OTHER PUBLICATIONS

"International Application Serial No. PCT/JP2021/00798, International Search Report dated Apr. 13, 2021", w/ English Translation, (Apr. 13, 2021), 5 pgs.

*Primary Examiner* — Ashley L Fishback
(74) *Attorney, Agent, or Firm* — Schwegman Lundberg & Woessner, P.A.

(57)          ABSTRACT

An ultrasonic treatment instrument includes: a vibration transmitter main body having a proximal end to which a vibration generation source is connected; a first support in which a central axis of an outer peripheral surface of the first support is shifted from a central axis of an inner peripheral surface of the first support when an external force is not applied; a second support in which a central axis of an outer peripheral surface of second support coincides with a central axis of an inner peripheral surface of second support when the external force is not applied; and a tubular portion into which the vibration transmitter is inserted and which has an inner peripheral surface on which the first support and the second support abut.

17 Claims, 9 Drawing Sheets

ULTRASONIC TREATMENT INSTRUMENT

CROSS-REFERENCE TO RELATED APPLICATION

This application is a continuation of International Application No. PCT/JP2021/007980, filed on Mar. 2, 2021, the entire contents of which are incorporated herein by reference.

BACKGROUND

1. Technical Field

The present disclosure relates to an ultrasonic treatment instrument.

2. Related Art

In the related art, there is known an ultrasonic treatment instrument that applies ultrasonic energy to a site to be treated (hereinafter referred to as a target site) in a biological tissue, thereby treating the target site (e.g., refer to WO 2017/119099 A).

The ultrasonic treatment instrument described in WO 2017/119099 A includes an ultrasonic transducer, a vibration transmitter, a liner member, and a shaft portion, which will be described below.

The ultrasonic transducer generates ultrasonic vibration.

The vibration transmitter has a proximal end connected to the ultrasonic transducer, and transmits ultrasonic vibration from the proximal end toward a distal end thereof.

The liner material is provided on the outer peripheral surface of the vibration transmitter main body and has an annular shape.

The shaft portion has a tubular shape, into which the vibration transmitter main body is inserted and which has an inner peripheral surface on which a support abuts.

SUMMARY

In some embodiments, an ultrasonic treatment instrument includes: a vibration transmitter main body having a proximal end to which a vibration generation source configured to generate ultrasonic vibration is connected, the vibration transmitter main body being configured to transmit ultrasonic vibration from the proximal end toward a distal end of the vibration transmitter main body; a first support in which a central axis of an outer peripheral surface of the first support is shifted from a central axis of an inner peripheral surface of the first support when an external force is not applied; a second support in which a central axis of an outer peripheral surface of second support coincides with a central axis of an inner peripheral surface of second support when the external force is not applied; and a tubular portion into which the vibration transmitter is inserted and which has an inner peripheral surface on which the first support and the second support abut, the vibration transmitter main body being disposed inside the tubular portion in a state of being elastically deformed by application of the external force.

In some embodiments, an ultrasonic treatment instrument includes: a vibration transmitter main body having a proximal end to which a vibration generation source configured to generate ultrasonic vibration is connected, the vibration transmitter main body being configured to transmit ultrasonic vibration from the proximal end toward a distal end of the vibration transmitter main body; a support which is provided on an outer peripheral surface of the vibration transmitter main body and has an annular shape; and a tubular portion into which the vibration transmitter is inserted and which has an inner peripheral surface on which the support abuts, the vibration transmitter main body being disposed inside the tubular portion in a state of being elastically deformed by an external force that is generated by positioning the tubular portion in a state where a central axis of the vibration generation source and a central axis of the tubular portion are shifted from each other.

In some embodiments, an ultrasonic treatment instrument includes: a vibration transmitter main body having a proximal end to which a vibration generation source that generates ultrasonic vibration is connected, the vibration transmitter main body being configured to transmit ultrasonic vibration from the proximal end toward a distal end of the vibration transmitter main body; a support which is provided on an outer peripheral surface of the vibration transmitter main body and has an annular shape; and a tubular portion into which the vibration transmitter is inserted and which has an inner peripheral surface on which the support abuts, the tubular portion having a partially bent shape, the vibration transmitter main body being disposed inside the tubular portion in a state of being elastically deformed by an external force that is generated by disposing the vibration transmitter main body inside the tubular portion.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 2 is a cross-sectional view illustrating a transducer unit;

DETAILED DESCRIPTION

Figure 1:
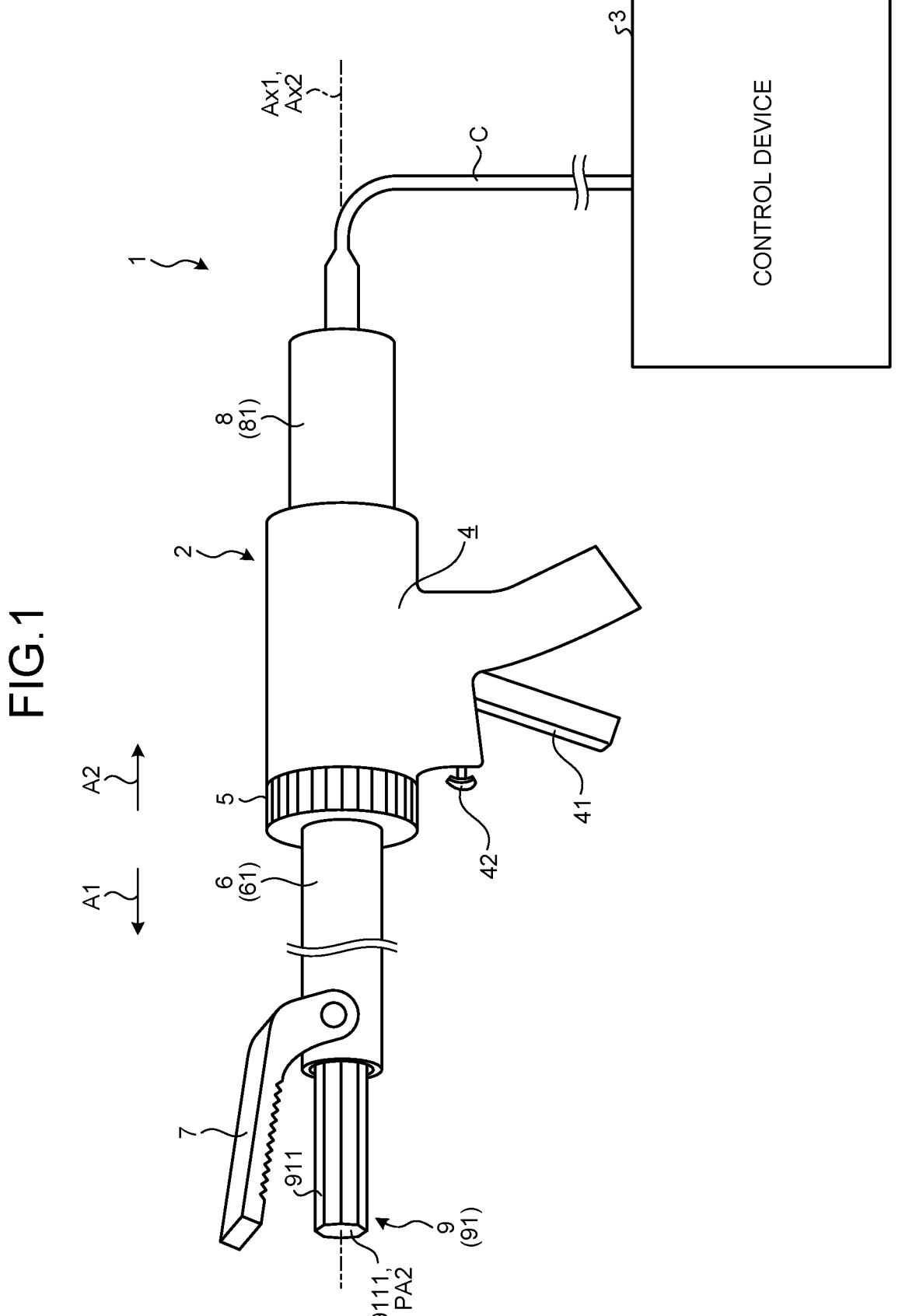
FIG. 1 is a diagram illustrating a treatment system according to a first embodiment.

Modes for carrying out the disclosure (hereinafter, embodiments) will be described below with reference to the drawings. Note that the disclosure is not limited to the embodiments described below. Further, in the description of the drawings, the same portions are denoted by the same reference numerals.

First Embodiment

Schematic Configuration of Treatment System FIG. 1 is a diagram illustrating a treatment system 1 according to a first embodiment.

The treatment system 1 applies ultrasonic energy and high-frequency energy to a site to be treated (hereinafter referred to as a target site) in a biological tissue, thereby treating the target site. The treatment means, for example, coagulation and incision of a target site. As illustrated in FIG. 1, the treatment system 1 includes an ultrasonic treatment instrument 2 and a control device 3.

The ultrasonic treatment instrument 2 is, for example, a medical treatment instrument using a bolted Langevin transducer (BLT) for treating a target site in a state of being passed through an abdominal wall. As illustrated in FIG. 1, the ultrasonic treatment instrument 2 includes a handle 4, a rotary knob 5, a tubular portion 6, a jaw 7, a transducer unit 8, and a vibration transmitter 9.

Note that in the following, a central axis of a sheath 61 constituting the tubular portion 6 is referred to as a central axis Ax1 (FIG. 1). In the following, one side along the central axis Ax1 will be referred to as a distal end side A1 (FIG. 1), and the other side will be referred to as a proximal end side A2 (FIG. 1).

The handle 4 is a portion to be held by a hand of a practitioner. As illustrated in FIG. 1, the handle 4 is provided with an operation knob 41 and an operation button 42.

The rotary knob 5 has a substantially cylindrical shape coaxial with the central axis Ax1, and as illustrated in FIG. 1, is provided at an end portion on the distal end side A1 of the handle 4. The rotary knob 5 receives a rotation operation by an operator such as a practitioner. The rotation operation rotates the rotary knob 5 about the central axis Ax1 with respect to the handle 4. The rotation of the rotary knob 5 rotates the sheath 61, the jaw 7, and the vibration transmitter 9 about the central axis Ax1.

Figure 3:
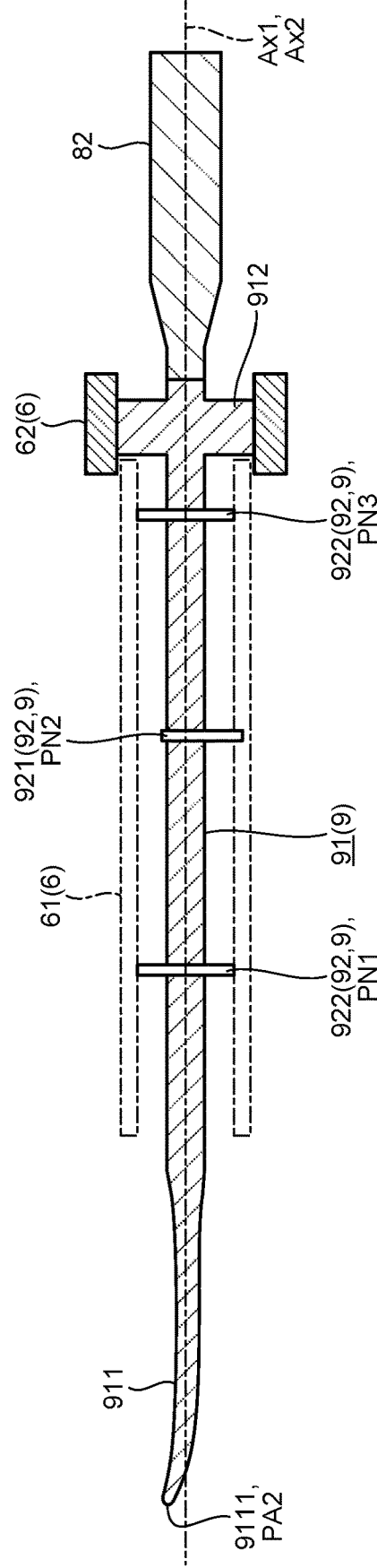
FIG. 3 is a diagram for explaining the elastic deformation of a vibration transmitter main body.
Figure 4:
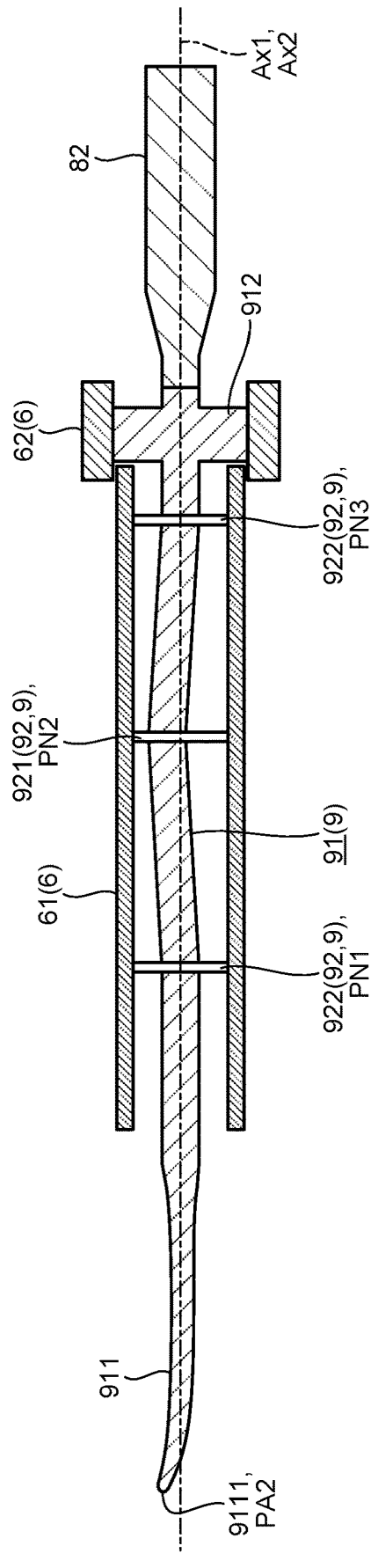
FIG. 4 is a diagram for explaining the elastic deformation of the vibration transmitter main body.

The tubular portion 6 includes the sheath 61 (see FIG. 1) and a fixing portion 62 (see FIGS. 3 and 4).

In the first embodiment, the sheath 61 has a cylindrical shape extending linearly. The sheath 61 has a portion on the proximal end side A2 inserted into the handle 4 from the distal end side A1 of the handle 4.

Note that the configuration of the fixing portion 62 will be described in "Configuration of Vibration Transmitter" to be described later.

In the following, a central axis of an ultrasonic transducer portion 82 constituting the transducer unit 8 is referred to as a central axis Ax2 (see FIG. 2).

Figure 2:
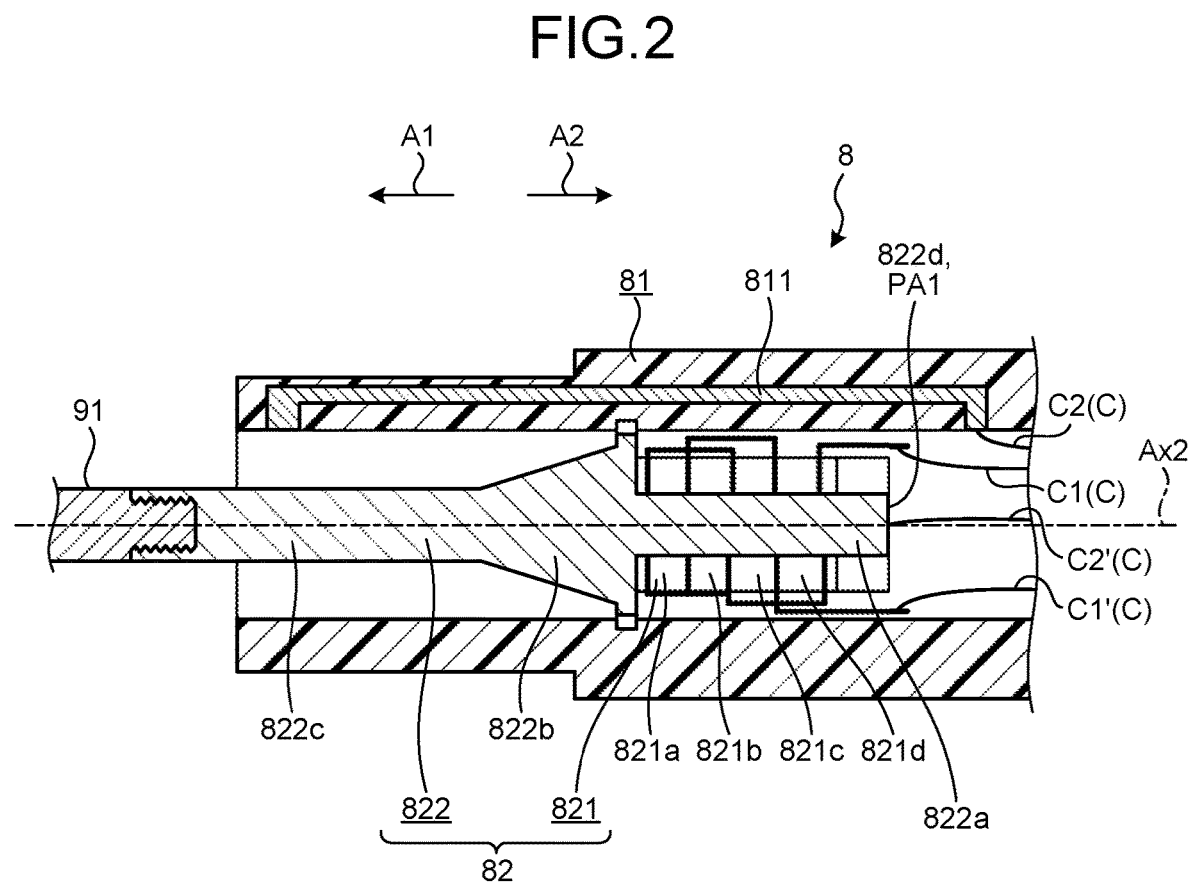

FIG. 2 is a cross-sectional view illustrating the transducer unit 8. Specifically, FIG. 2 is a cross-sectional view of the transducer unit 8 taken along a plane including the central axis Ax2.

As illustrated in FIG. 2, the transducer unit 8 includes a transducer casing 81 and an ultrasonic transducer portion 82.

The transducer casing 81 extends linearly along the central axis Ax2, and is attached to the handle 4 by a portion on the distal end side A1 of the transducer casing being inserted into the handle 4 from the proximal end side A2 of the handle 4.

The ultrasonic transducer portion 82 corresponds to a vibration generation source. The ultrasonic transducer portion 82 is housed inside the transducer casing 81 and generates ultrasonic vibration under the control of the control device 3. As illustrated in FIG. 2, the ultrasonic transducer portion 82 includes an ultrasonic transducer 821 and a horn 822.

The ultrasonic transducer 821 is a portion that generates ultrasonic vibration. In the first embodiment, the ultrasonic transducer 821 is a BLT including a plurality of piezoelectric elements 821a to 821d stacked along the central axis Ax2. Note that in the first embodiment, the ultrasonic transducer 821 includes four piezoelectric elements 821a to 821d, but the number of piezoelectric elements is not limited to four, and may be another number.

The horn 822 is a portion that enlarges the amplitude of the ultrasonic vibration generated by the ultrasonic transducer 821. The horn 822 has a long shape extending linearly along the central axis Ax2. As illustrated in FIG. 2, the horn 822 has a configuration in which a first mounting portion 822a, a cross-sectional area changing portion 822b, and a second mounting portion 822c are arranged from the proximal end side A2 to the distal end side A1.

The first mounting portion 822a is a portion on which the ultrasonic transducer 821 is mounted.

The cross-sectional area changing portion 822b has a shape whose cross-sectional area decreases toward the distal end side A1, and is a portion that enlarges the amplitude of ultrasonic vibration.

The second mounting portion 822c is a portion on which the vibration transmitter 9 is mounted.

The jaw 7 and the vibration transmitter 9 are portions that grasp a target site and apply ultrasonic energy and high-frequency energy to the target site, thereby treating the target site.

Note that the configuration of the vibration transmitter 9 will be described in "Configuration of Vibration Transmitter" to be described later.

The jaw 7 is rotatably attached to the end portion on the distal end side A1 of the sheath 61, and grasps the target site between the jaw and a treatment portion 911 (FIG. 1) of the vibration transmitter 9. Note that inside the handle 4 and the sheath 61 described above, an opening/closing mechanism (not illustrated) is provided to open and close the jaw 7 with respect to the treatment portion 911 in accordance with the operation of the operation knob 41 by a practitioner. In the first embodiment, the jaw 7 is partially formed of an electrically conductive material.

The control device 3 is electrically connected to the ultrasonic treatment instrument 2 by an electric cable C (FIG. 1), and integrally controls the operation of the ultrasonic treatment instrument 2.

As illustrated in FIG. 2, a pair of transducer lead wires C1 and C1' constituting the electric cable C is joined to the ultrasonic transducer 821.

As illustrated in FIG. 2, the transducer casing 81 is provided with a first conductive portion 811 that extends from an end portion on the proximal end side A2 to an end portion on the distal end side A1. Although a specific illustration is omitted, the sheath 61 is provided with a second conductive portion that extends from an end portion on the proximal end side A2 to an end portion on the distal end side A1 and electrically connects the first conductive portion 811 and the jaw 7. Further, a high-frequency lead wire C2 constituting the electric cable C is joined to an end portion on the proximal end side A2 of the first conductive portion 811. A high-frequency lead wire C2' constituting the electric cable C is joined to the first mounting portion 822a.

The control device 3 operates as follows when the operation button 42 is pressed by the practitioner.

The control device 3 supplies AC power to the ultrasonic transducer 821 via the pair of transducer lead wires C1 and C1'. Thus, the ultrasonic transducer 821 generates ultrasonic vibration. The ultrasonic vibration is transmitted from the proximal end of the vibration transmitter 9 to the treatment portion 911 by the vibration transmitter 9. Ultrasonic vibration is applied from the treatment portion 911 to the target site grasped between the jaw 7 and the treatment portion 911. In other words, ultrasonic energy is applied to the target site.

The control device 3 supplies high-frequency power between the jaw 7 and a vibration transmitter main body 91 (treatment portion 911) formed of an electrically conductive material constituting the vibration transmitter 9 via the pair of high-frequency lead wires C2 and C2', the first conductive portion 811, the second conductive portion, and the horn 822. Thus, a high-frequency current flows through the target site grasped between the jaw 7 and the treatment portion 911. In other words, high-frequency energy is applied to the target site.

Configuration of Vibration Transmitter

A detailed configuration of the vibration transmitter 9 will now be described.

Figure 5:
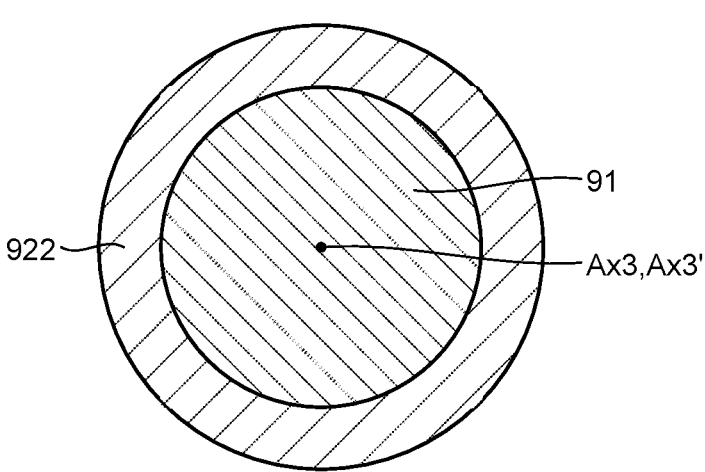
FIG. 5 is a diagram for explaining the elastic deformation of the vibration transmitter main body.
Figure 6:
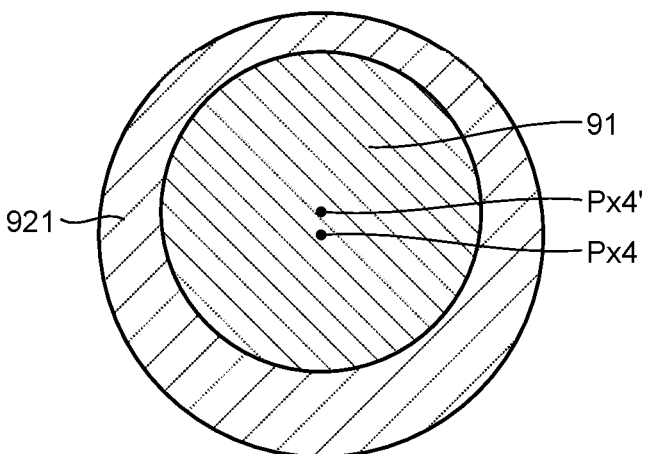
FIG. 6 is a diagram for explaining the elastic deformation of the vibration transmitter main body.

FIGS. 3 to 6 are diagrams for explaining the elastic deformation of the vibration transmitter main body 91. Specifically, FIGS. 3 and 4 are cross-sectional views of the sheath 61, the vibration transmitter 9, and the ultrasonic transducer portion 82 taken along a plane including the central axes Ax1 and Ax2. Note that FIG. 3 illustrates a state before the sheath 61 is attached. Therefore, in FIG. 3, the sheath 61 is indicated by a dashed-and-dotted line. FIG. 4 illustrates a state after the sheath 61 is attached. FIG. 5 is a cross-sectional view of the vibration transmitter 9 taken along a plane orthogonal to the central axes Ax1 and Ax2 at a position PN1 illustrated in FIG. 4. FIG. 6 is a cross-sectional view of the vibration transmitter 9 taken along a plane orthogonal to the central axes Ax1 and Ax2 at a position PN2 illustrated in FIG. 4.

As illustrated in FIG. 3 or 4, the vibration transmitter 9 includes the vibration transmitter main body 91 and a support 92.

The vibration transmitter main body 91 is formed of, for example, an electrically conductive material such as titanium alloys, and as illustrated in FIG. 3 or 4, has a long shape extending substantially linearly along the central axis Ax1. As illustrated in FIG. 1, the vibration transmitter main body 91 is inserted into the sheath 61 in a state where a portion on the distal end side A1 protrudes outward. In the following, the end portion on the distal end side A1 is referred to as a treatment portion 911. As illustrated in FIG. 2, an end portion on the proximal end side A2 of the vibration transmitter main body 91 is connected to the second mounting portion 822c. The vibration transmitter main body 91 transmits the ultrasonic vibration generated by the ultrasonic transducer 821 and passed through the horn 822 from the end portion on the proximal end side A2 to the treatment portion 911, and applies the ultrasonic vibration to the target site grasped between the treatment portion 911 and the jaw 7, thereby treating the target site.

The vibration transmitter main body 91 and the ultrasonic transducer portion 82 serve as one vibrating body that performs longitudinal vibration by ultrasonic vibration at a predetermined resonance frequency generated by the ultrasonic transducer 821. Therefore, an end surface 822d (FIG. 2) on the proximal end side A2 of the horn 822 is located at a position PA1 (FIG. 2) on the most proximal end side A2 among the positions of the antinodes of longitudinal vibration. An end surface 9111 (FIGS. 3 and 4) on the distal end side A1 of the vibration transmitter main body 91 is located at a position PA2 (FIGS. 3 and 4) on the most distal end side A1 among the positions of the antinodes of longitudinal vibration. Note that the longitudinal vibration has a frequency of, for example, 47 kHz and an amplitude at the position PA2 of, for example, 80 μm.

In the vibration transmitter main body 91, the treatment portion 911 is a portion located on the distal end side with respect to the position PN1 on the most distal end side A1 among the positions PN1 to PN3 (FIGS. 3 and 4) of the nodes of longitudinal vibration. In the first embodiment, the treatment portion 911 is curved as illustrated in FIG. 3 or 4. More specifically, the treatment portion 911 has a shape bent along a horizontal plane orthogonal to an opening and closing direction in which the jaw 7 opens and closes with respect to the treatment portion 911 toward the distal end side A1. Note that in FIG. 1, for convenience of description, the treatment portion 911 is illustrated in a shape extending linearly without being curved.

In the vibration transmitter main body 91, the end portion on the proximal end side A2 is formed with an annular flange portion 912 projecting outward as illustrated in FIG. 3 or 4.

The fixing portion 62 has a cylindrical shape, and is positioned inside the handle 4 while supporting the flange portion 912 inside the fixing portion. In other words, the vibration transmitter main body 91 is fixed inside the handle 4 while being positioned by the fixing portion 62. As illustrated in FIG. 3 or 4, an end portion on the proximal end side A2 of the sheath 61 is inserted into the fixing portion 62, and positioning of the sheath 61 is also performed in the fixing portion. In other words, in the positioned state, the central axis Ax1 of the sheath 61 coincides with the central axis Ax2 of the ultrasonic transducer portion 82 as illustrated in FIG. 4.

In the first embodiment, the support 92 is formed of an elastic rubber material, and is an annular lining (liner material) into which the vibration transmitter main body 91 is inserted. More specifically, the supports 92 are respectively disposed at the positions PN1 to PN3 of the nodes of longitudinal vibration on the outer peripheral surface of the vibration transmitter main body 91. The outer peripheral surface of the support 92 abuts on the inner peripheral surface of the sheath 61 in a state where the vibration transmitter 9 is inserted into the sheath 61. As illustrated in FIG. 3 or 4, the support 92 includes a first support 921 and two second supports 922.

The two second supports 922 are linings disposed at the positions PN1 and PN3, respectively. These two second supports 922 have the same shape, and as illustrated in FIG. 5, the central axis Ax3 of the outer peripheral surface and the central axis Ax3' of the inner peripheral surface coincide with each other.

The first support 921 is a lining disposed at the position PN2. The position PN2 is a position (e.g., the position of the antinode of transverse vibration) other than the position of the node of the transverse vibration generated in the vibration transmitter main body 91 by the ultrasonic vibration generated by the ultrasonic transducer 821. As illustrated in FIG. 6, the first support 921 has the central axis Ax4 of the outer peripheral surface and the central axis Ax4' of the inner peripheral surface shifted from each other. In the first embodiment, the central axis Ax4' is shifted in the curved direction (upward in FIGS. 3, 4, and 6) of the treatment portion 911 with respect to the central axis Ax4.

Since the support 92 is provided as described above, the vibration transmitter main body 91 is disposed inside the sheath 61 in the following state.

In other words, the two second supports 922 are disposed inside the sheath 61 in a state where the central axis Ax3' coincides with the central axes Ax1 and Ax2. On the other hand, the first support 921 is disposed inside the sheath 61 in a state where the central axis Ax4' is shifted in the curved direction of the treatment portion 911 with respect to the central axes Ax1 and Ax2. Thus, as illustrated in FIG. 4, at the position PN2, the vibration transmitter main body 91 is disposed inside the sheath 61 in a state of being elastically deformed by an external force being applied from the first support 921 in the curved direction of the treatment portion 911. In other words, the vibration transmitter main body 91 is flexed at the position PN2.

According to the first embodiment described above, the following effects are obtained.

In the ultrasonic treatment instrument 2 according to the first embodiment, the vibration transmitter main body 91 is disposed inside the sheath 61 in a state of being elastically deformed by an external force being applied from the first support 921. In other words, by applying an external force to the vibration transmitter main body 91 to elastically deform the vibration transmitter main body, the transverse vibration generated in the vibration transmitter main body 91 by the ultrasonic vibration generated by the ultrasonic transducer 821 is attenuated.

Accordingly, the ultrasonic treatment instrument 2 according to the first embodiment can attenuate vibration (transverse vibration) other than desired vibration (longitudinal vibration). Therefore, the generation of abnormal noise and the like caused by the transverse vibration can also be suppressed.

In particular, the first support 921 is provided at the position PN2 which is a position (e.g., the position of the antinode of transverse vibration) other than the position of the node of transverse vibration.

Therefore, by applying an external force to the vibration transmitter main body 91 at the position PN2, the transverse vibration can be effectively attenuated.

The vibration direction of transverse vibration may be the same as the curved direction of the treatment portion 911.

In the ultrasonic treatment instrument 2 according to the first embodiment, an external force is applied to the vibration transmitter main body 91 along the curved direction of the treatment portion 911.

Therefore, the transverse vibration can be attenuated more effectively.

Second Embodiment

The second embodiment will now be described.

In the following description, the same components as those of the first embodiment described above are denoted by the same reference numerals, and detailed description thereof will be omitted or simplified.

In the first embodiment described above, the vibration transmitter main body 91 is disposed inside the sheath 61 in an elastically deformed state by using the first support 921.

On the other hand, in the second embodiment, the vibration transmitter main body 91 is disposed inside the sheath 61 in an elastically deformed state without using the first support 921.

Figure 7:
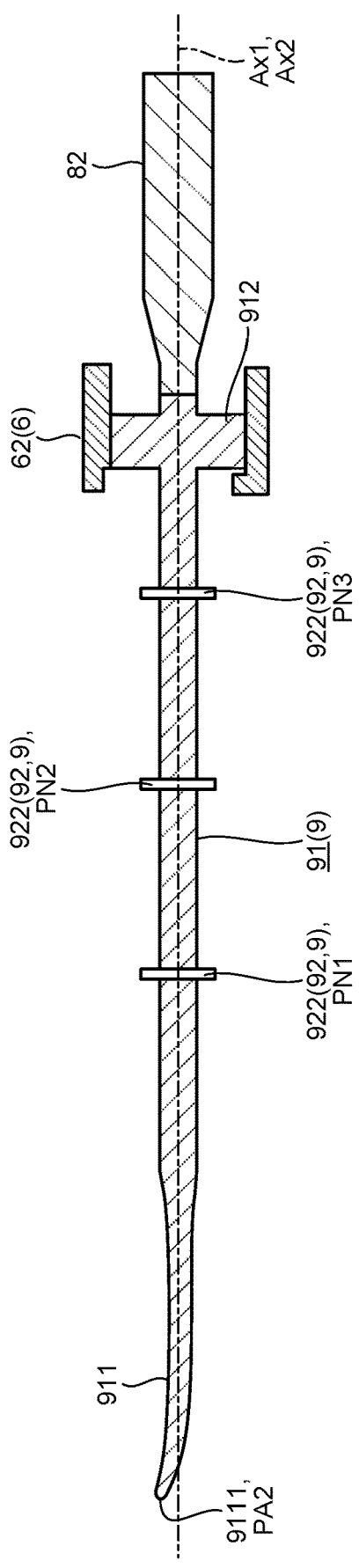
FIG. 7 is a diagram for explaining the elastic deformation of a vibration transmitter main body according to a second embodiment.
Figure 8:
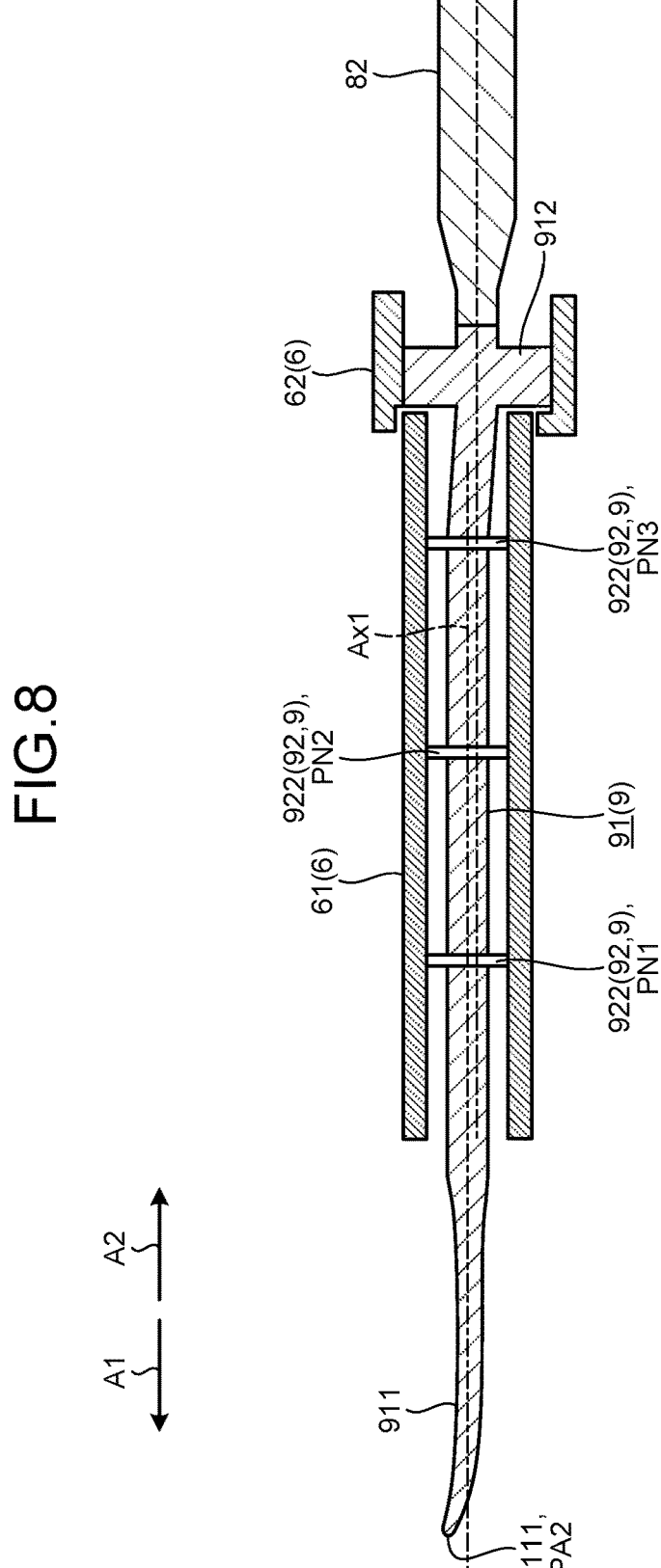
FIG. 8 is a diagram for explaining the elastic deformation of the vibration transmitter main body according to the second embodiment.

FIGS. 7 and 8 are diagrams for explaining the elastic deformation of the vibration transmitter main body 91. Specifically, FIG. 7 is a diagram corresponding to FIG. 3. FIG. 8 is a diagram corresponding to FIG. 4.

As illustrated in FIG. 7 or 8, the support 92 according to the second embodiment employs a second support 922 instead of the first support 921 in the support 92 described in the first embodiment described above. In other words, all three of the supports 92 according to the second embodiment are constituted of the second supports 922.

As illustrated in FIG. 7, the fixing portion 62 according to the second embodiment performs positioning of the sheath 61 in a state where the central axis Ax1 of the sheath 61 is shifted from the central axis Ax2 of the ultrasonic transducer portion 82. In the second embodiment, since the positioning is performed, the central axis Ax1 is shifted in the curved direction of the treatment portion 911 with respect to the central axis Ax2.

Since the positioning of the sheath 61 is performed by the fixing portion 62 as described above, the vibration transmitter main body 91 is disposed inside the sheath 61 in the following state.

In other words, the three second supports 922 are disposed inside the sheath 61 in a state where the central axis Ax3' coincides with the central axis Ax1. In other words, the three second supports 922 are disposed inside the sheath 61 in a state where the central axis Ax3' is shifted in the curved direction of the treatment portion 911 with respect to the central axis Ax2 of the ultrasonic transducer portion 82. Thus, the vibration transmitter main body 91 is disposed inside the sheath 61 in a state of being elastically deformed by an external force applied along the curved direction of the treatment portion 911 through the support 92 from the sheath 61 in which the central axis Ax1 is shifted from the central axis Ax2. In other words, the vibration transmitter main body 91 flexes at a portion on the proximal end side A2 with respect to the second support 922 located on the most proximal end side A2.

Even when the vibration transmitter main body 91 is elastically deformed as in the second embodiment described above, the same effects as those of the first embodiment described above are obtained.

Third Embodiment

The third embodiment will now be described.

In the following description, the same components as those of the first embodiment described above are denoted by the same reference numerals, and detailed description thereof will be omitted or simplified.

In the first embodiment described above, the vibration transmitter main body 91 is disposed inside the sheath 61 in an elastically deformed state by using the first support 921.

On the other hand, in the third embodiment, the vibration transmitter main body 91 is disposed inside the sheath 61 in an elastically deformed state without using the first support 921.

Figure 9:
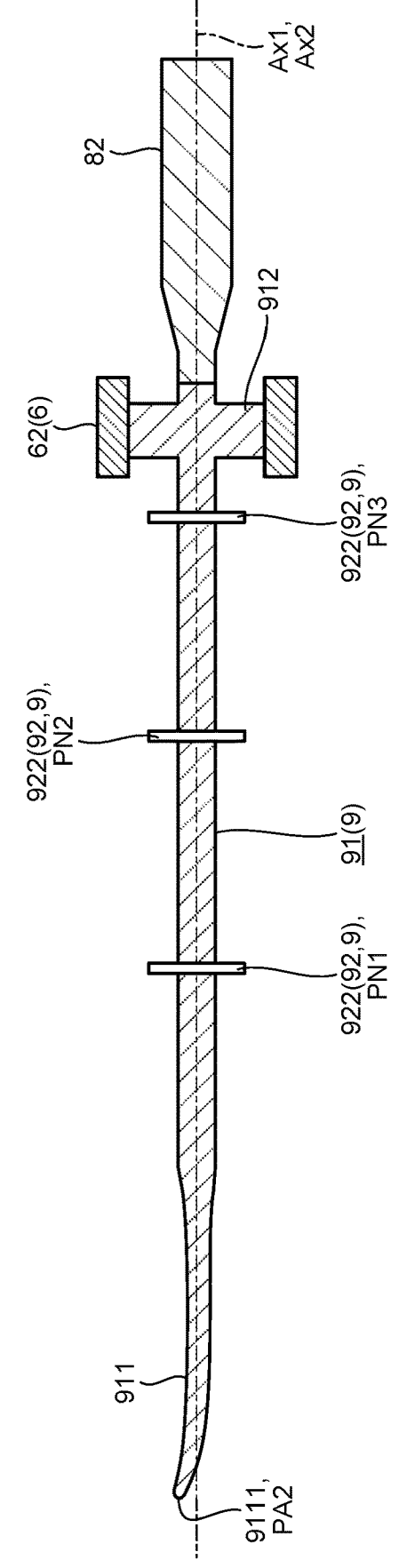
FIG. 9 is a diagram for explaining the elastic deformation of a vibration transmitter main body according to a third embodiment.
Figure 10:
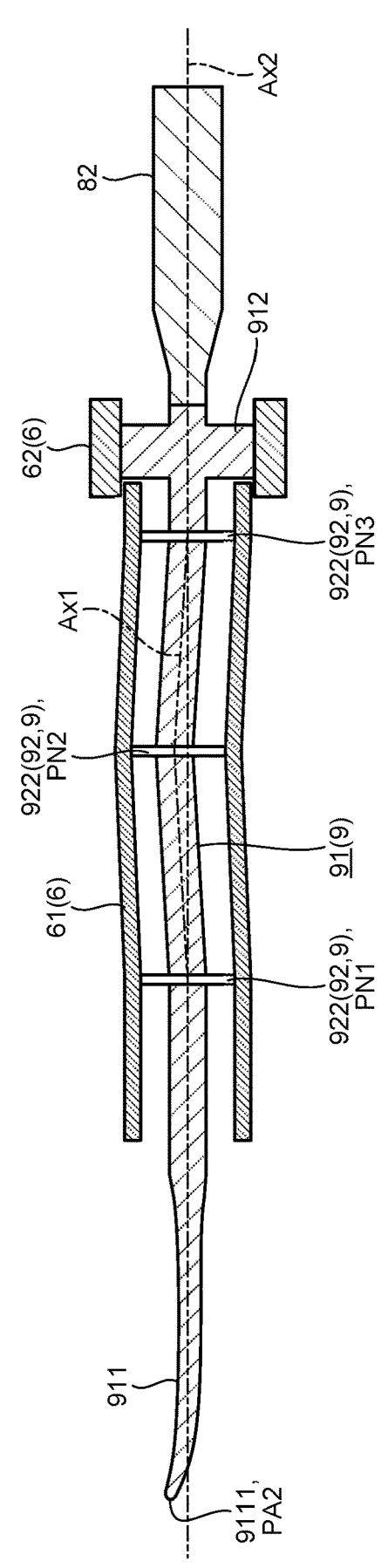
FIG. 10 is a diagram for explaining the elastic deformation of the vibration transmitter main body according to the third embodiment.

FIGS. 9 and 10 are diagrams for explaining the elastic deformation of the vibration transmitter main body 91. Specifically, FIG. 9 is a diagram corresponding to FIG. 3. FIG. 10 is a diagram corresponding to FIG. 4.

As illustrated in FIG. 9 or 10, the support 92 according to the third embodiment employs a second support 922 instead of the first support 921 in the support 92 described in the first embodiment described above. In other words, all three of the supports 92 according to the third embodiment are constituted of the second supports 922.

As illustrated in FIG. 10, the sheath 61 according to the third embodiment has a cylindrical shape extending in a partially bent and curved shape. In other words, in a state where the sheath 61 is positioned on the fixing portion 62, the central axis Ax1 is shifted from the central axis Ax2 of the ultrasonic transducer portion 82 as illustrated in FIG. 10. In the third embodiment, the central axis Ax1 is shifted in the curved direction of the treatment portion 911 with respect to the central axis Ax2 only in a portion including the position PN2, while the central axis Ax1 coincide with the central axis Ax2 in other portions.

Since the sheath 61 is bent as described above, the vibration transmitter main body 91 is disposed inside the sheath 61 in the following state.

In other words, the three second supports 922 are disposed inside the sheath 61 in a state where the central axis Ax3' coincides with the central axis Ax1. In other words, the two second supports 922 located at the positions PN1 and PN3 among the three second supports 922 are disposed inside the sheath 61 in a state where the central axis Ax3' coincides with the central axis Ax2. On the other hand, the one second support 922 located at the position PN2 is disposed inside the sheath 61 in a state where the central axis Ax3' is shifted in the curved direction of the treatment portion 911 with respect to the central axis Ax2. Thus, the vibration transmitter main body 91 is disposed inside the sheath 61 in a state of being elastically deformed by an external force applied from the bent sheath 61 through the support 92 along the curved direction of the treatment portion 911. In other words, the vibration transmitter main body 91 flexes at the peripheral portion of the position PN2.

Even when the vibration transmitter main body 91 is elastically deformed as in the third embodiment described above, the same effects as those of the first embodiment described above are obtained.

Other Embodiments

While the embodiments for carrying out the disclosure have been described above, the disclosure should not be limited only to the first to third embodiments described above.

Although the first embodiment described above employs a configuration in which both ultrasonic energy and high-frequency energy are applied to the target site, the embodiment is not limited thereto, and may employ a configuration in which only ultrasonic energy is applied. Further, the first embodiment may employ a configuration in which at least one of high-frequency energy and thermal energy by a heater or the like is applied in addition to ultrasonic energy.

In the first to third embodiments described above, the external force is applied to the vibration transmitter main body 91 along the curved direction of the treatment portion 911, but the embodiments are not limited thereto, and the external force may be applied along a direction opposite to the curved direction of the treatment portion 911, or the external force may be applied along other directions.

Although the first embodiment described above employs the support 92 which is a lining as the support (first support), the embodiment is not limited thereto. For example, the first embodiment may employ the flange portion 912 as the support (first support). For example, the central axis of the flange portion 912 is set at a position shifted from the central axis Ax2 of the ultrasonic transducer portion 82. Thus, an external force is applied to the vibration transmitter main body 91 at the position of the flange portion 912, and the vibration transmitter main body is elastically deformed (flexed).

In the first embodiment described above, only one first support is provided among all the supports 92, but the embodiment is not limited thereto, and two or more first supports may be provided. In this case, the two or more first supports may have the same shape, or may be configured such that the shift amount or the shift direction of the central axis Ax4' with respect to the central axis Ax4 is different.

According to an ultrasonic treatment instrument and a vibration transmitter according to the disclosure, vibration other than desired vibration can be attenuated.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment instrument comprising:
   a vibration rod configured to transmit ultrasonic vibration from a proximal end of vibration rod toward a distal end of the vibration rod;
   a tube into which the vibration rod is inserted;
   a first support having a first through hole in a longitudinal direction of the vibration rod, an outer surface of the first support abutting an inner surface of the tube; and
   a second support having a second through hole in the longitudinal direction of the vibration rod, an outer surface of the second support abutting the inner surface of the tube wherein:
   the vibration rod is inserted into the first support and the second support; and
   the first through hole has a center of the first through hole, the second through hole has a center of the second through hole, and the center of the first through hole is offset relative to the center of the second through hole.

2. The ultrasonic treatment instrument according to claim 1, wherein an external force is a force applied to the vibration rod from the first support and the second support.

3. The ultrasonic treatment instrument according to claim 2, wherein the vibration rod is disposed inside the tube in a state of being elastically deformed by application of the external force.

4. The ultrasonic treatment instrument according to claim 1, wherein the first support is disposed at a position other than a position of a node of transverse vibration of the vibration rod by the ultrasonic vibration.

5. The ultrasonic treatment instrument according to claim 1, wherein a plurality of second supports are provided.

6. The ultrasonic treatment instrument according to claim 5, wherein the first support is located between the plurality of second supports.

7. The ultrasonic treatment instrument according to claim 1, wherein each of the first support and the second support is formed of an elastic rubber material.

8. The ultrasonic treatment instrument according to claim 1, wherein each of the first support and the second support is disposed at a node position of longitudinal vibration of the vibration rod by the ultrasonic vibration.

9. The ultrasonic treatment instrument according to claim 1, wherein the vibration rod includes a treatment portion located at a distal end of the vibration rod and is curved, and wherein an external force is applied to the vibration rod along a curved direction of the treatment portion.

10. The ultrasonic treatment instrument according to claim 1, wherein the center of the first through hole is offset relative to a central axis of the tube.

11. An ultrasonic treatment instrument comprising:
    a vibration rod configured to transmit ultrasonic vibration from a proximal end of the vibration rod toward a distal end of the vibration rod;

a support having a through hole, the vibration rod inserted into the through hole; and a tube into which the vibration rod is inserted, an inner surface of the tube abutting an outer surface of the support, wherein the vibration rod is elastically deformed by an external force generated in a state where a central axis of the through hole and a central axis of the tube are shifted from each other.

12. The ultrasonic treatment instrument according to claim 11, wherein the external force is applied to the vibration rod from the support.

13. The ultrasonic treatment instrument according to claim 11, wherein the support is disposed at a position other than a position of a node of transverse vibration of the vibration rod by the ultrasonic vibration.

14. An ultrasonic treatment instrument comprising:

a vibration rod configured to transmit ultrasonic vibration from a proximal end of the vibration rod toward a distal end of the vibration rod;

a support located on an outer peripheral surface of the vibration rod, wherein the support is disposed at a node position of longitudinal vibration of the vibration rod by the ultrasonic vibration; and a tube into which the vibration rod is inserted, which has an inner surface of the tube abutting the support, the tube having a partially bent shape, wherein the vibration rod is elastically deformed by an external force generated by disposing the vibration rod and the support inside the tube.

15. The ultrasonic treatment instrument according to claim 14, wherein a support has a through hole, wherein the through hole has a center of the through hole, and wherein the center of the through hole is offset relative to a central axis of the tube.

16. The ultrasonic treatment instrument according to claim 14, wherein the external force is applied to the vibration rod from the support.

17. The ultrasonic treatment instrument according to claim 14, wherein the support is disposed at a position other than a position of a node of transverse vibration of the vibration rod by the ultrasonic vibration.

* * * * *